(12) United States Patent
Heller

(10) Patent No.: US 8,686,863 B2
(45) Date of Patent: Apr. 1, 2014

(54) SYSTEM AND PROCESS FOR DETECTING A FEBRILE CONDITION

(71) Applicant: Alan C. Heller, Dallas, TX (US)

(72) Inventor: Alan C. Heller, Dallas, TX (US)

( * ) Notice: Subject to any disclaimer, the term of this patent is extended or adjusted under 35 U.S.C. 154(b) by 0 days.

(21) Appl. No.: 13/685,574

(22) Filed: Nov. 26, 2012

(65) Prior Publication Data

US 2013/0085409 A1 Apr. 4, 2013

Related U.S. Application Data

(63) Continuation-in-part of application No. 13/161,771, filed on Jun. 16, 2011.

(51) Int. Cl.
*G08B 23/00* (2006.01)

(52) U.S. Cl.
USPC ... 340/573.1; 340/584; 340/603; 340/539.12; 340/573.5

(58) Field of Classification Search
USPC ............... 340/573.1, 603, 584, 539.12, 573.5
See application file for complete search history.

(56) References Cited

U.S. PATENT DOCUMENTS

| | | | | |
|---|---|---|---|---|
| 5,299,594 A | * | 4/1994 | Lord et al. | 137/101.19 |
| 5,339,687 A | * | 8/1994 | Gimson et al. | 73/204.19 |
| 5,499,631 A | * | 3/1996 | Weiland | 600/547 |
| 6,677,859 B1 | * | 1/2004 | Bensen | 340/604 |
| 2004/0220538 A1 | * | 11/2004 | Panopoulos | 604/361 |
| 2009/0284380 A1 | * | 11/2009 | Chen et al. | 340/584 |
| 2011/0050432 A1 | * | 3/2011 | MacSween et al. | 340/603 |

* cited by examiner

*Primary Examiner* — Travis Hunnings
(74) *Attorney, Agent, or Firm* — John Lindsay

(57) ABSTRACT

The invention is directed to a system and process for estimating a core body temperature of a human subject. The system includes mount, a body, and a heat trap having a temperature sensor. The mount is operable to secure the device to a toilet or adjacent surface. The body houses a microprocessor. The heat trap is distal to the body and is shaped to receive a liquid stream and contain the thermal energy therein. The heat trap comprises a low thermally conductive material. The temperature sensor is in communication with the microprocessor. The temperature sensor is associated with the heat trap and disposed proximate a surface of said heat trap, wherein the liquid stream is directed across said temperature sensor. The system optionally incorporates a process and memory to store input of the temperature sensor and associate the input with a person, compare the input to historical records for a person, and determine a febrile condition for the person based on the input.

18 Claims, 8 Drawing Sheets

SYSTEM AND PROCESS FOR DETECTING A FEBRILE CONDITION

PRIORITY

This patent application claims priority to U.S. patent application Ser. No. 13/161,771 filed Jun. 16, 2011, which is hereby incorporated by reference.

BACKGROUND

1. Field of the Invention

The technology relates to systems for determining a febrile condition in a human subject, and more particularly, to systems for determining a febrile condition in a human subject by collecting and processing temperature data from liquid excretions.

2. Description of the Related Art

It has been become increasingly necessary to detect and identify people that may be infected with a contagious illness, whether bacterial or viral. People are very mobile, traveling from city to city and country to country, and that factor makes it even more important to identify infected persons, to prevent or at least minimize the potential for the spread of disease. In recent years there has been mounting concern about such international infectious diseases as SARS in recent years, and concerns about infections transmitted in hospitals, where patients may be screened upon ingress but do not exhibit detectable conditions at that time. There is a consensus that elimination of transmission of a contagion through detection and isolation of infected individuals may be an effective tool in avoiding the spread of the contagion. However, there does not appear to be a ready solution to the issue of identification of the infected individual.

It is well known that most infectious diseases produce an increase in core body temperature in the host. This is often also the earliest sign of the infection. Accordingly, measuring core body temperature and monitoring it in facilities such as work places, hospitals, school, and other places where large numbers of people congregate or interact may pose a potential for identifying and isolating potentially infected persons and preventing or reducing the risk of transmission of the infection. Additionally, periodic measurements of core body temperature increases the possibility of detecting core body temperature changes earlier than would otherwise occur.

Measuring core body temperature, unlike measurement of body surface temperature, poses several challenges, however. Core body temperature measurements are typically taken in an invasive procedure, for example, use of an oral thermometer, or infra-red device inserted into an ear cavity. Accordingly, it is challenging to carry out such monitoring on a periodic basis for large groups of people. Indeed, it is quite likely that individuals may resist such procedures. The core body temperature poses challenges as well because core body temperature varies from one individual to another as an inherent condition of the individual. But, for each individual, core body temperature will increase when an infectious agent is present and the body's defenses are activated in response. Thus, core body temperature is a much better indicator of infection for an individual and may be used with a high degree of confidence for that individual when there is a reliable "baseline" of temperature data for that individual.

SUMMARY

An exemplary embodiment provides a system for identifying individuals and screening the individuals for a febrile condition. The invention is directed to a system and process for estimating a core body temperature of a human subject. The system includes mount, a body, and a heat trap having a temperature sensor. The mount is operable to secure the device to a toilet or adjacent surface. The body houses a microprocessor. The heat trap is distal to the body and is shaped to receive a liquid stream and contain the thermal energy therein. The heat trap comprises a low thermally conductive material. The temperature sensor is in communication with the microprocessor. The temperature sensor is associated with the heat trap and disposed proximate a surface of said heat trap, wherein the liquid stream is directed across said temperature sensor. The system optionally incorporates an identity system to facilitate association of temperature sensor data with a person. Further, the system optionally incorporates a processor and memory to store input of the temperature sensor and associate the temperature input with a person, compare the input to historical records for the person, and determine a febrile condition for the person based on the temperature input.

BRIEF DESCRIPTION OF THE DRAWINGS

The following drawings are not to scale and are provided for ease of explanation. The figures depict exemplary embodiments, and do not limit the scope of the invention, as defined in the claims; here below:

DETAILED DESCRIPTION

Figure 1:
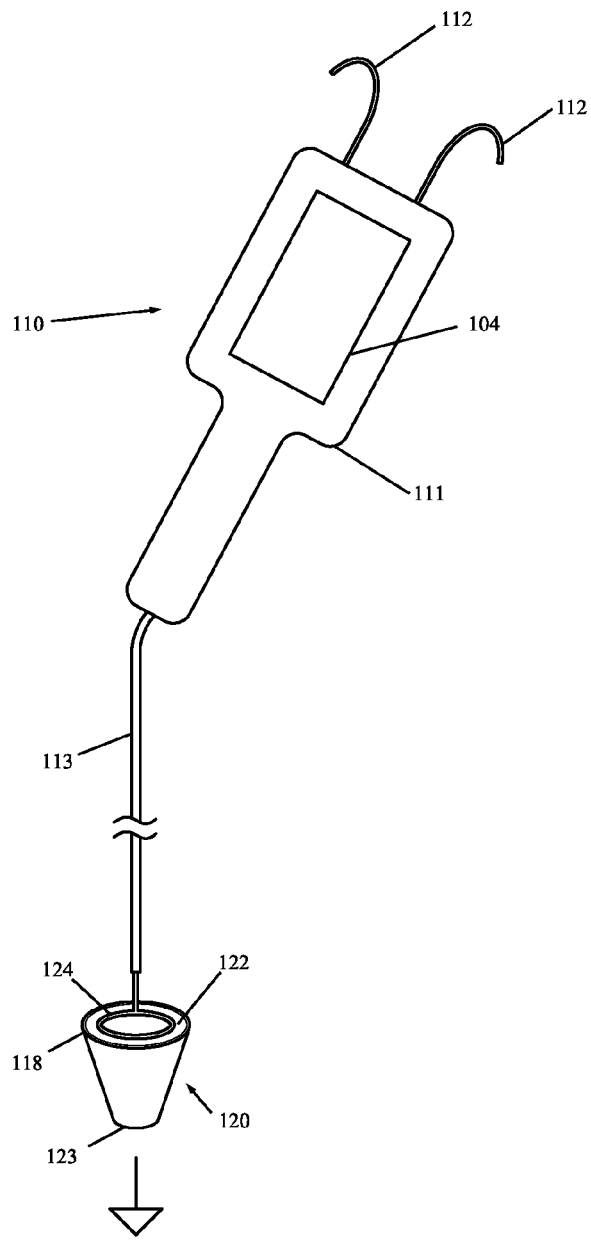
FIG. 1 depicts an embodiment of a core body temperature urine monitor.

The following detailed description provides a description of exemplary embodiments of the technology claimed here below to facilitate an understanding of the technology, but does not limit the scope of the technology claimed.

As a preliminary matter, there are several factors that may, or ought, to be taken into account in making a determination about whether an individual is exhibiting a febrile condition. A key factor is the person's core body temperature (TC). However, TC varies from one individual to another, and is therefore not precisely constant for all persons, although 98.6° F. is regarded as "normal," i.e. not febrile. A more accurate determination of whether a person has a febrile condition is to accumulate a database of that person's temperature over a period of time and to obtain a baseline or cluster of TC from that data for that individual. Excursions from that base TC could then be assessed statistically as to any upward or downward trend with a degree of confidence regarding whether that particular person has a TC outside of his/her own normal range. However reading TC is often invasive, and requires both the time of the individual and a professional, as well as close human contact and object contact. When using a professional person to detect temperature and using a contact measurement protocol for population screening on a large scale where (it is anticipated) that the substantial majority of the subjects are not febrile, it creates cross contamination issues, risking the spread of infection. This risk of spreading the infection may be greater than what the screening process was designed to prevent, under these circumstances. The costs, inconvenience, time, and cross contamination problems create both a real and/or perceived diminishing return for such a large scale effort.

In women, body temperature changes during the ovulation cycle, with the peak typically occurring at ovulation. It is within the spirit of this invention to monitor fertility and to adjust the febrility determination based on the ovulation cycle.

The disclosed examples of the inventive technologies address these temperature-related issues and bring solutions to some commonly encountered situations. For example, it is desirable in many facilities, such as hospitals and nursing homes, to minimize risks of spreading any kind of infectious illness. One way of addressing that issue is to identify febrile persons and to take steps to either exclude those persons from the facility or take other suitable precautions. Additionally, due to the incubation period of a pathogen and the delayed onset of the immune response contributing to the febrile condition, an additional way of addressing that issue to periodically monitor persons for febrile conditions within the facility in order to either remove those persons from the facility or take other suitable precautions. Thus, examples of a "gate-keeper" technology of identification, temperature detection, and febrile condition determination are presented.

Skin temperatures can be measured but these are far less reliable as indicia of a febrile condition because human bodies release heat and also adjust the heat released based on ambient temperature conditions. However, a close correlation exists between urinary bladder liquid temperatures and TC, especially at the moment urine from the bladder is excreted from the body.

Referring now to FIG. 1, the core body temperature urine monitor 110 has a mount 112, a body 111, and at least one heat trap 120 incorporating a temperature sensor 124.

The mount 112 is operable to secure the core body temperature urine monitor 110 to a toilet 108 or adjacent surface. The depicted mount 112 includes a pair of semi-rigid, flexible wires 112 secured to the core body temperature urine monitor 110. A first end of each of the wires 112 is affixed to the body 111. The flexible wires' 112 flexibility enables a user to deform the wires 112 according to the mounting surface of the toilet 108 or other adjacent surface, while the semi-rigidity aids securing the body 111 to the mounting surface. An alternate embodiment can employ a different mechanical fastener or a chemical fastener such as glue.

The body 112 preferably houses a microprocessor 130, display 104, and other electronics for receiving and processing data from the temperature sensor 124.

The core body temperature urine monitor 110 includes at least one heat trap 120 incorporating a temperature sensor 124. The term "heat trap" means a structure that is designed to receive incoming thermal energy, trap that thermal energy and minimize losses of thermal energy from its structure. The heat trap is preferably composed of a material that is resistant to thermal energy passing through it (i.e. it is a "thermally insulative" material, or a "low thermal conductivity" material). Optionally, the heat trap can include an inner thermally reflective surface that may include a coating or lining of a heat reflective material. The heat trap is operable to receive a portion of the urine stream 106, containing the thermal energy therein.

Figure 2:
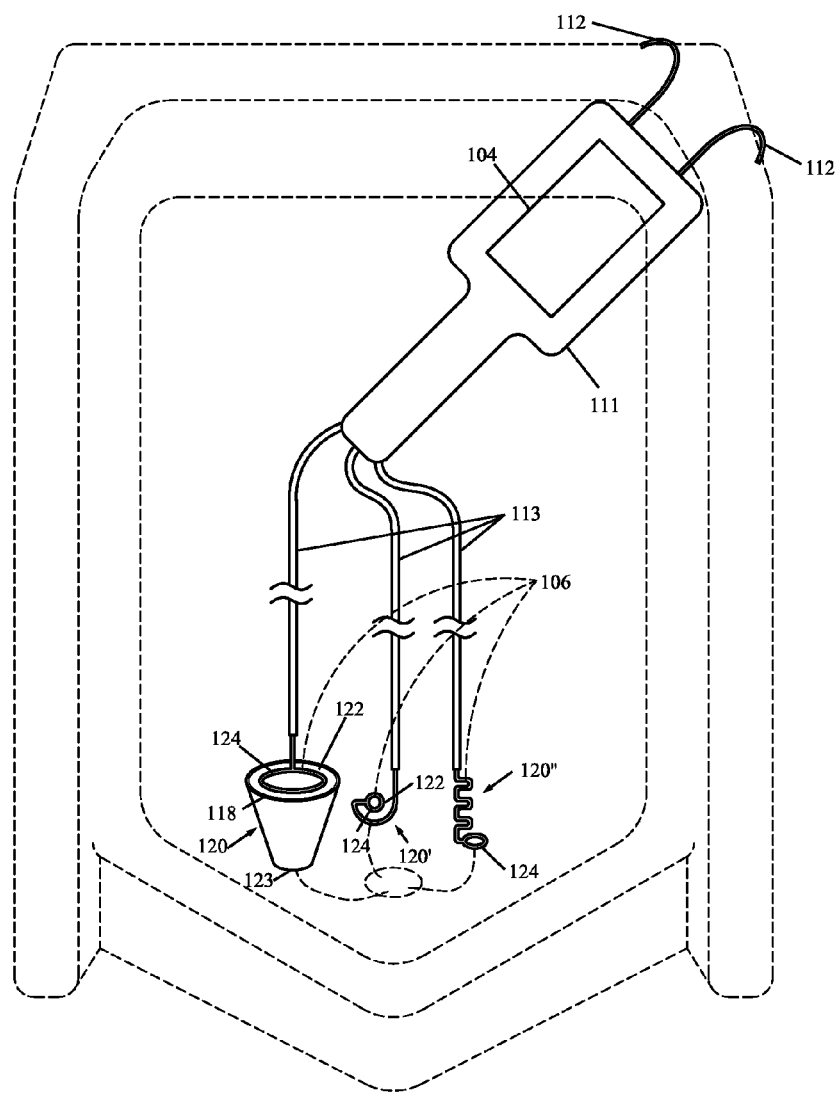
FIG. 2 depicts a frontal view of an alternate embodiment of a core body temperature urine monitor.
Figure 3:
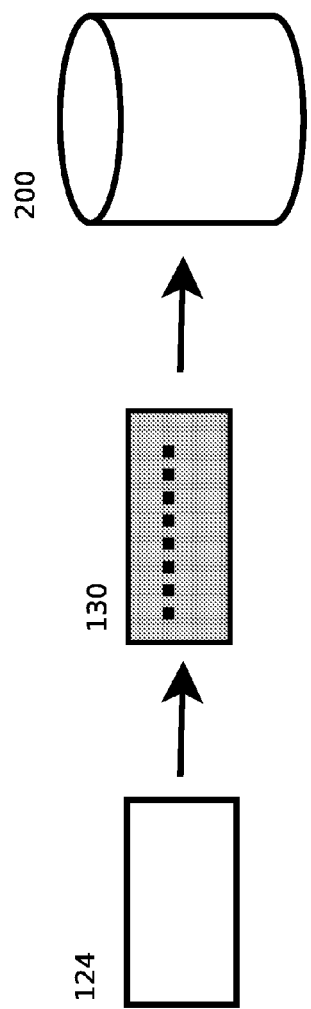
FIG. 3 depicts a block diagram showing an embodiment of a core body temperature urine monitor.

Referring to FIG. 2, multiple configurations of the heat trap 120 120' 120" are illustrated. Heat trap 120 is a generally cup shaped sidewall 121, including an upper section having an opening 122 and a lower section having an outlet 123. The sidewall 121 forms a perimeter enclosing the region from the opening 122 to the outlet 123. The enclosed region defines a passage for a urine stream 106. Preferably, the width of the passage tapers from its upper section to its lower section, whereby the width of opening 122 is greater than the width of the outlet 123. The depicted heat trap 120 has an inverse frustroconical cross profile, although other shapes are in the spirit of this invention.

The heat trap 120 is optionally incorporates a heat reflective inner surface 126 of the sidewall 121. This surface 126 may be created by the adhering of a material such as a metalized biaxially-oriented polyethylene terephthalate (Bo-PET) film, for example, metallized MYLAR® film [MYLAR is a registered trademark of DuPont Tejjin Films of Chester, Va.]. Other examples of an inner reflective surface include, but are not limited to, metallic foils and the like. In addition, as an alternative, the inner surface 126 may simply be of a sprayed on reflective metallic paint, such as aluminum, gold, copper, silver, and the like. Additionally, heat trap 120 optionally incorporates a hydrophilic inner surface 126 in order to alter liquid flow. The inner surface 126 may be coated or impregnated with hydrophilic substances such as silica based compounds or the like. The hydrophilic substance may be occasionally replaced.

A temperature sensor 124 is disposed within or proximate the enclosed region of the heat trap 120.

An alternately configured heat trap 120' is a generally "U" channel shaped strip. The strip has a curvilinear cross-profile, including a downwardly depending section adjacent to an upwardly depending section. The adjacent downwardly and upwardly depending sections define a partial perimeter and present a channel through which liquid can flow. The depicted heat trap 120' has a "U" shaped cross profile, although other profiles may be employed in this configuration. This alternately configured heat trap 120' can also optionally incorporate a heat reflective inner surface 126 or a hydrophilic inner surface 126. A temperature sensor is 124 is disposed within or proximate the channel of the heat trap 120'.

An alternately configured heat trap 120" includes a ridged surface. The strip includes a downwardly depending section having at least one ridge 115 rising from its surface operable to alter liquid flow across the strip. The strip is preferably mounted slightly askew from a completely vertical orientation. That is to say that a plane presented by the strip is at an acute angle relative to the downward gravitational force. The ridges 115 on the surface of the strip may vary in height relative to each other in order to alter liquid flow rate across its surface. This alternately configured heat trap 120" can also optionally incorporate a heat reflective surface 126 or a hydrophilic surface 126. A temperature sensor is 124 is disposed on or proximate the surface of the heat trap 120".

It is within the spirit of this invention that one or more heat traps 120 120' 120" of one or more configurations can be employed in a single unit.

When a liquid stream 106 flows through the heat trap 120, the liquid and thermal energy is contained. In practice, of course, there are always minor heat losses from the heat trap 120. But, with an efficient heat trap 120, the heat flow out of the trap will be minimized so that the temperature within the heat trap will closely approximate or equal the core body temperature within the limits of accuracy required and/or provided by suitable temperature sensors.

Figure 4:
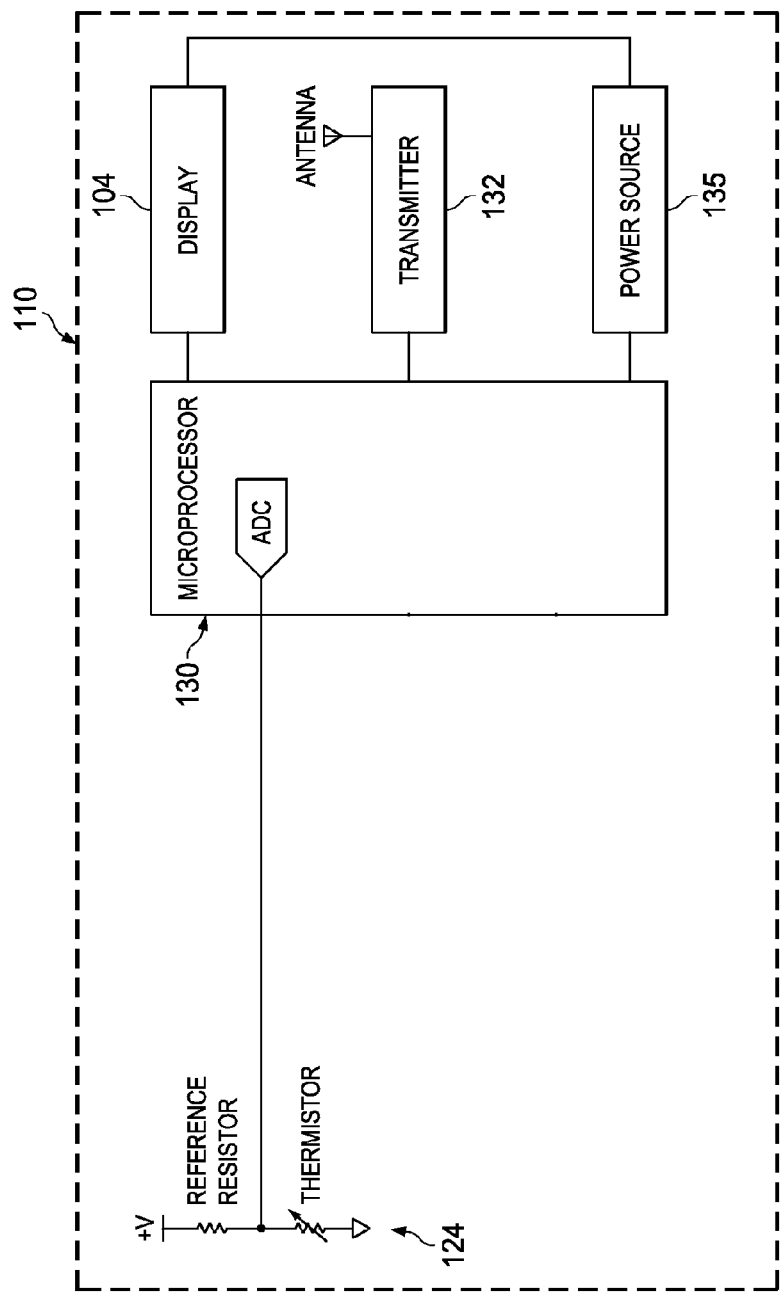
FIG. 4 depicts a block diagram showing electronic detail for an embodiment of a core body temperature urine monitor.

To measure the temperature TT in the heat trap 120, the exemplary embodiments of FIGS. 1 and 2 employ an associated temperature sensor 124. As shown in FIG. 4, the sensor 124 is in communication with a microprocessor 130. The communication can occur via a wire 113, retractable wire 113, or wirelessly. The temperature sensor 124 may be a thermistor, a thermocouple, or any other suitable sensor that can provide temperature input to a microprocessor 130, with or without signal conversion from analog to digital. Microprocessor 130 communicates the sensed temperature to the transmitter 132, also shown in FIG. 4.

Optionally, the system adjusts the received temperature prior to further use in order to compensate for possible heat loss of the liquid in transit from the body to the heat trap 120 and at the heat trap 120. The system may adjust the received temperature based on the heat capacity of water, heat capacity of urine, heat capacity of the hygroscopic substance, heat capacity of the heat trap 120, evaporative heat loss, distance from the heat trap 120, or other factors. The system may incorporate additional apparatus for such adjustments. For example, the system can incorporate a distance sensor for detection of the distance of the users from the heat trap 120.

Optionally, as shown in FIGS. 1 and 2, the urine temperature monitor 110 may have a display panel 104. The microprocessor 130 is in communication with this display panel 104 to provide input for temperature display.

The exemplary embodiment of the system includes an identity system to facilitate identification of the user whose liquid excrement is being measured. The identity system facilitates association of temperature data with a user. The system can employ facial recognition, RFID readers, bar code scanners and other means in the art. A first identity system includes a camera 826 mounted proximate the toilet and a person database. The camera 826 sends optical data to a server comparison to the person database. An alternate identity system includes an RFID reader mounted proximate the toilet in communication with a person database. An RFID reader detects the identified user associated with the RFID of the user in order to create the association between the user and the temperature input. Another alternate identity system includes a bar code reader mounted proximate the toilet in communication with a person database. The bar code reader communicates the identified user associated with the bar code borne by the user in order to create the association between the user and the temperature input.

In order to determine with a higher level of confidence whether the user has a fever, it is desirable to have a series of core body temperature readings of that individual over a period of-time at useful intervals. The period of time may be all the time that the user is in an environment where he or she must be monitored, or any other time. However, these readings should be accumulated in a database 220 and the readings should be subjected to analysis to estimate with a high degree of confidence whether the user has a fever. An exemplary database 220 may include a separate file for each person to be monitored. The file contains information about the person's identity, including, but not limited to, any or all of: name, contact information, and identity system data. In addition the person's file may include temperature data, such as: previous raw temperature readings, adjusted temperature readings, estimate core body temperature readings, and time at which these temperatures were taken, ambient temperature, and a heat trap identifier.

In an exemplary embodiment, as mentioned, the urine temperature monitor 110 is supplied with a memory operable to store data, including time and temperature readings, in a database 220. Further, the urine temperature monitor 110 may be supplied with a processor able to execute a calculation to determine core body temperature. When a core body temperature deviation from the normal is of sufficient magnitude that is predetermined to justify a determination of a significant risk of febrile condition, the urine temperature monitor 110 may indicate an alarm condition audibly, visually, electronically, or otherwise. In addition, it may transmit a signal to alert appropriate parties.

Figure 5:
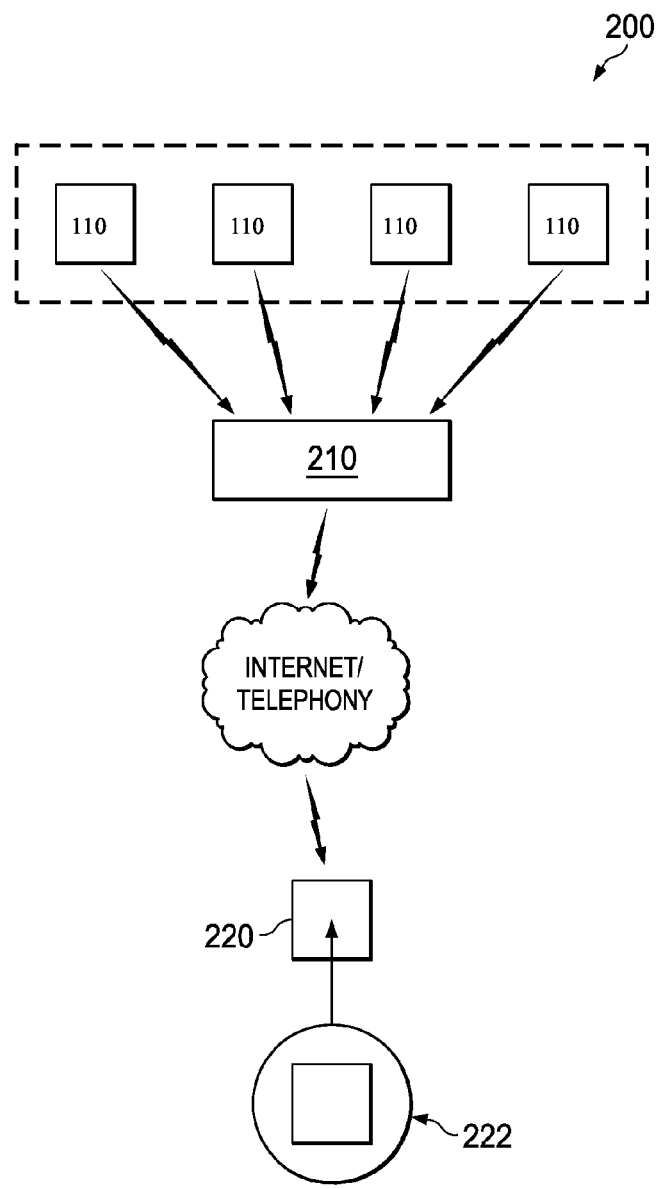
FIG. 5 depicts a diagram showing an embodiment of a system incorporating plural heat traps.
Figure 6:
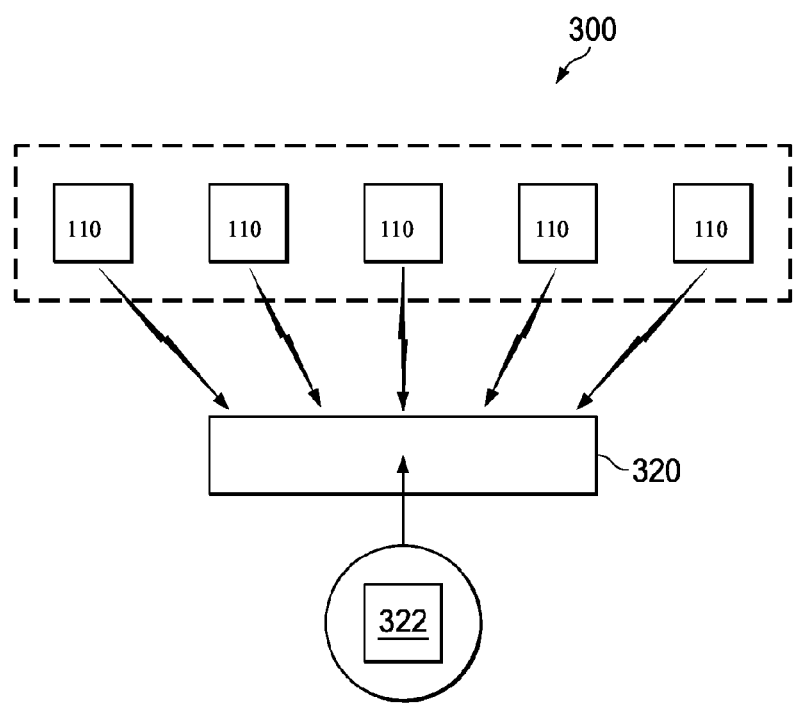
FIG. 6 depicts a diagram showing another embodiment of a system using core body temperature urine monitors to monitor core body temperatures of a plurality of individuals.

Two exemplary systems for monitoring core body temperature of urine temperature monitor 110 users are shown in FIGS. 5 and 6. However, other systems are also useful to accumulate user temperature data and to determine whether or not the wearer has a fever.

In the example of FIG. 5, the system 200 includes urine temperature monitors 110 (100 now) transmitting information to a receiver-transmitter 210. The transmitting of information may be by any suitable wireless protocol. Desirably, to conserve urine temperature monitor 110 power, the transmission is of a kind that minimizes power usage. Non-limiting examples include Bluetooth, WiMax, digital telephony, and the like wireless protocols. The information transmitted includes the time and the sensed temperatures. Of course, other data may also be transmitted, if required or desirable. The receiver-transmitter 210 in turn transmits the information to a server (computer) 220, for example, via WiFi over the Internet, Bluetooth, telephony (e.g. 3G or 4g systems) or any other wireless protocol suitable under the circumstances.

The server 220 includes a database 222 in its memory. An exemplary database includes a separate segment for each user that also has fields for input of new information as received from the receiver—transmitter 210, and storing this information for processing. The information from the database is processed to determine whether a user, identified by his database file, has a fever.

In an alternative example of a system 300, the receiver-transmitter 210 is not necessary. Instead, the urine temperature monitors 110 transmit information directly to the server 320 that has a database 322. The transmission protocols may be selected for suitability of purpose and the power supply and power usage for the monitors 110. The database 320 may be like database 220 described above, and the calculations to estimate fever may be the same or similar.

The database 220 is organized by the unique identity of the sensor 124 paired to a unique identity of the person. This arrangement in the database permits reuse of the sensor by other individuals as well as the ability to view any measurement biases that a given sensor 124 may be exhibiting across different individuals. Thus, if necessary action may be taken to compensate for any known tendencies of a particular sensor 124. The schema for the database is extensive, covering historical records for all individuals on a historic basis in a single day's record as well as a table of current measurements for every individual. The database records also include the current reader identity so as to give information on the physical proximate location of the sensor in the network.

In a further aspect, the technology is also directed toward controlling the access of persons having a detected febrile condition to a particular facility, which may be a hospital, nursing home, school, place of work, manufacturing facility, or indeed any place where such screening may be deemed useful or necessary. Exemplary embodiments of this aspect are illustrated in FIGS. 7 and 8.

Figure 7:
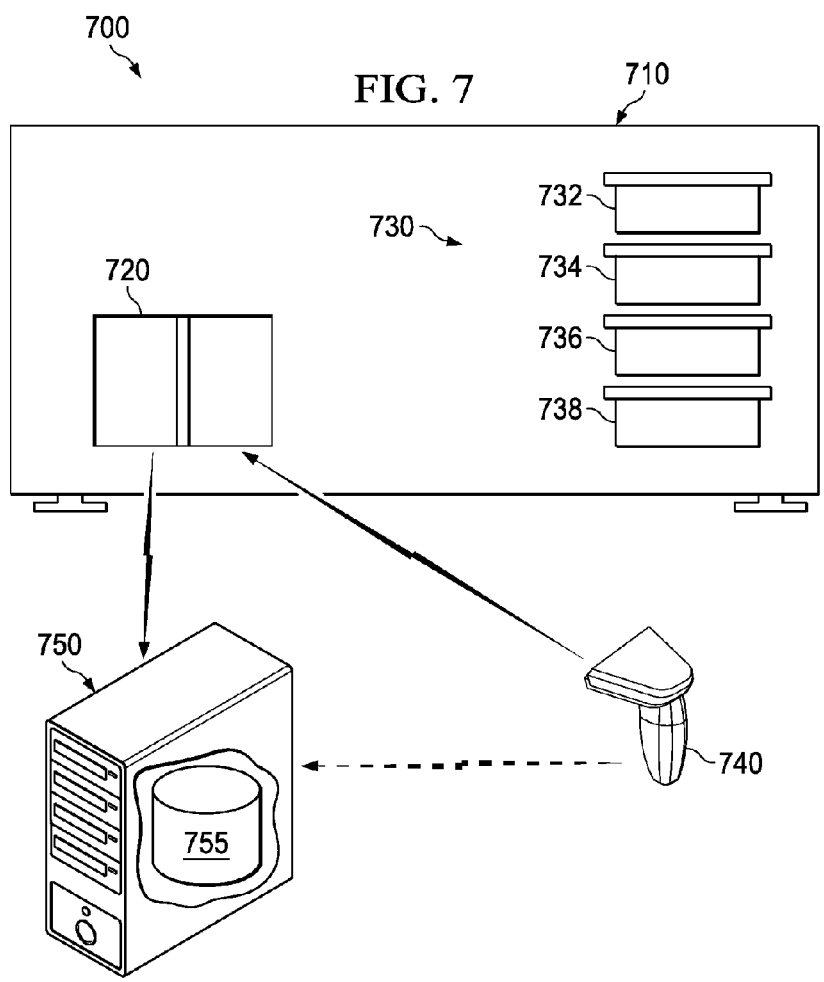
FIG. 7 depicts an embodiment of a system for screening and identifying persons with a febrile condition.
Figure 8:
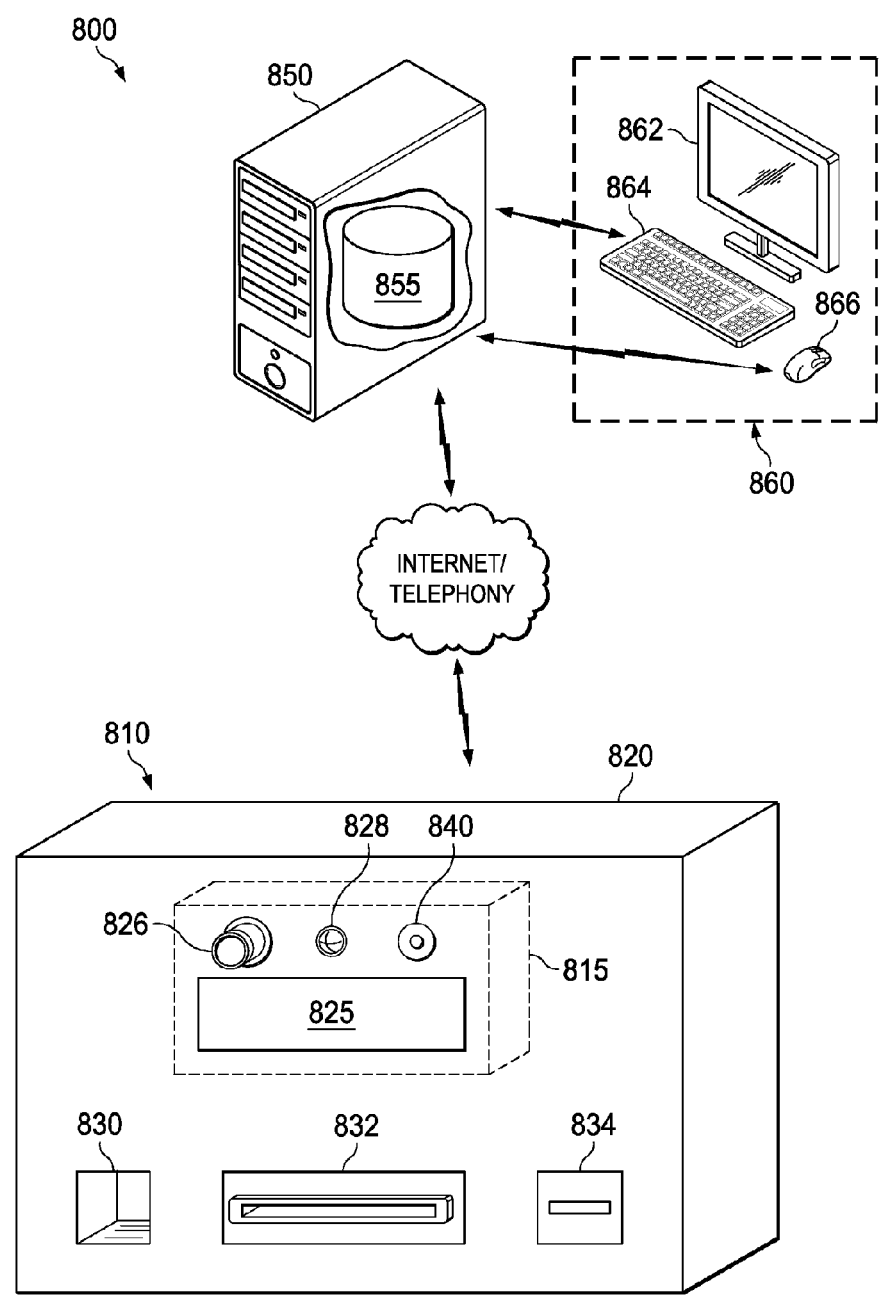
FIG. 8 depicts an alternate embodiment of a system for screening and identifying persons with a febrile condition.

FIG. 7 illustrates an exemplary system 700 for screening and identifying persons with a febrile condition, preferably located at a restroom entrance of a protected area in which febrile persons must either be identified, or from which they must be excluded, until further action may be taken, or to which they may be allowed access subject to restrictions. System 700 may include a station 710 to which is mounted a detector-transmitter 720 and a dispenser area 730. The dispenser area 730 may be compartmentalized or may include separate dispensers, such as a dispenser for gloves, a dispenser of tissue paper 734, a dispenser for masks 736, and a dispenser of a liquid or cream of an anti-bacterial formulation 738. The detector-transmitter 720 may include any of a bar code scanner, a RF detector for a smart card, and /or a biometric type of identifying device such as, for example, a hand/fingerprint scanner, a card reader, or an optical scanner that may be used to uniquely identify an individual and present indicia readable by the detector-transmitter 720. Further, the system 700 includes a temperature relay 740 with built in temperature data transmission capability. The temperature relay 740 is configured to selectively communicate with one or more of the heat trap 120 120' 120" technologies detailed above, or any other temperature detection technology that is accurate, precise, rapid and non-invasive. Temperature relay 740 may be releasably mounted to the station 710 by a holder 742. Temperature data from the temperature relay 740 may be transmitted to the detector-transmitter 720 via an RF transmitter, a Bluetooth transmitter or any other suitable transmitter. The detector-transmitter 720, which may be battery or electrically powered, transmits received data to a server 750, via the Internet by WIFI, by wired connection, by RF transmission, by Bluetooth transmission, WiMax, wireless telephony, or any other suitable mode of data transmission. Alternatively, the temperature relay 740 may transmit data directly to the server, if that is more convenient and the transmitter of the temperature relay 740 has the capability. The server 750 has a database 755 for compiling data about each of a plurality of individuals that are allowed access to the protected area, including pertinent data about their identities, respective scanning times for entry times at the facility, their temperatures, and other pertinent data, as necessary and useful for a particular facility.

The exemplary system 700 operates as follows: a person within the area that is being protected presents a form of identification readable by the detector-transmitter 720. This data is checked against the database 755 of server 750. If the person is authorized, with identifying data present in the database, he enters the restroom and proceeds to use a toilet. The sensed temperature, date and time is transmitted to the detector transmitter 720, or directly to the server 750, and recorded in the data file of that person in database 755. If a febrile condition is detected, an alarm (audible, visual, or electronic) is generated to notify responsible parties and a note may be placed in the person's data file in database 750. Detection of a febrile condition may be facilitated using the current sensed urine temperatures compared to prior temperature readings for that person. A person with temperature recording will be better detected for febrile condition or "outlier" from his/her normal temperature cluster. Such a person with a detected febrile condition or outlier may have his access restricted, allowed, or denied. Often the person may be guided by human resources guidelines that may dictate specified actions depending upon the job responsibility of the person. Greater protections, such as masks and gloves, may be required for personnel experiencing low grade fevers in ICU or kitchens as opposed to those persons working in other less critical areas.

As an added functionality, the system may optionally include a dispenser 730 from which the person seeking to enter the protected area may take gloves, masks, and tissues, and where he might clean his hands with an anti-bacterial formulation, before exiting.

In a further exemplary embodiment, a system 800, illustrated schematically in FIG. 8, includes a self-contained user-interface unit 810 that may be located at the entry point to a restroom within a facility which it is desired to exclude persons with a febrile condition, or at least identify them for alternative action. Such spaces may include, but are not limited to, hospitals, nursing homes, schools, places of business, manufacturing facilities, etc. Further, user interface unit. 810 may be enclosed within a housing 820 as shown in the example, or may be built into a convenient area in the vicinity of the entry point of the facility or department within the facility, such as a wall near an access doorway, as long as the components of the user-interface unit 810, described below, are accessible for maintenance and repair, as needed, and the function of the user-interface unit 810 is not impaired. The user interface unit 810 includes within housing 820 a "computer" 815 (shown in dashed lines), such as for example, a tablet PC or the equivalent, such as an iPad® (trademark of Apple, Inc. of Cupertino, Calif.) that has wireless capability, and a screen. In exemplary embodiments, the convenience of a tablet computer provides some advantages but, other devices may also be used. In other exemplary embodiments, the computer 815 may be selected from tablet devices using the Android™ operating system (product and trademark of Google of Mountainview, Calif.), Windows® (a registered trademark of Microsoft Corp. of Redmond, Wash.), or any other suitable operating systems. Preferably, but not necessarily, computer 815 may also have a front facing camera. Thus, the screen 825 of computer 815 is viewable and touchable (if a touch screen is used) through a window in housing 820. The screen may display several menus to guide a user through the identification, temperature detection and screening process.

The exemplary embodiment includes several alternative and optional features for recognizing a person seeking automated permission for access or to work in a facility protected by the system. These may include a camera, whether part of the computer 815 inside housing 820 or a separate camera, has a lens 826 that is able to capture data for facial recognition applications software technology. This facial recognition technology may be installed on the computer 815 to compare with facial data stored on a database on a memory on the computer 815 or at a remote database 855 on a server 850. Or, the application's software may be installed on a remote server 850 that has a database 855 with stored facial recognition data. The remote server 850 may be accessed in any of a number of ways: wirelessly via the internet, by hard wire connection, by local area network, and the like, as appropriate and convenient. Further, and optionally, in the event of dim light, a light source 828 is provided as well to assist facial recognition technology. A narrow beamed light may also be used to provide feedback on the video image from the camera regarding where the narrow beamed infrared sensor is currently aimed.

An individual seeking entry may also use a fingerprint ID pad 830 that collects data, and transmits it to a computer to identify the individual by comparing with stored data in a database. The applications software and fingerprint identification data for individuals may be stored either in the computer 815 in the housing 820 or at remote server 850, as described above in the case of facial recognition. The software user interface is designed to obviate the keyboard and minimize or eliminate touch, if possible. The addition of a fingerprint reader and software/camera based facial recognition minimizes this user touch. Presently, fingerprints are still far more consistently secure than facial recognition, by more than an order of magnitude. However, that situation is expected to change in the future as these technologies develop. Thus, only if the preset software confidence level of the facial recognition is insufficient for a presenting user, is the user asked for his/her fingerprint. This permits access with a single touch to the tiny fingerprint reader. The fingerprint access in turn positively reinforces the presenting face, which it did not provide a sufficiently high confidence level initially by itself to permit access.

In a further alternative, an individual issued with a tagged access card may identify by using a card reader 832. These card readers may be of any kind that is deemed suitable for the facility. For example an RF card reader, a bar code reader, a magnetic strip reader, and other reader suited to the type of card used by the facility. In addition, if upon identification of the individual, it is desired to predetermine the length of stay of that individual in the facility, the user interface unit 810 may include a time-sensitive tag dispenser so that this indicator may be displayed on the user's card to indicate the user's status as either "current" or "expired."

The identified person is linked to the sensed temperature from the urine temperature monitor 110. The result is compared with previous readings of TC for the particular individual. Based on the reading and the statistical distribution of readings for the particular individual in a non-febrile state, a determination can be made with a statistical confidence level as to whether the individual is febrile. The results may be displayed on screen 825, and may also be displayed at a remote location 860 equipped with a user interface, such as the illustrated exemplary monitor 862, keyboard 864 and mouse 866. Thus, an authorized individual may screen persons from entry (or take other action) based on both his or her identification credentials, as well as his or her temperature results as detected and calculated.

The foregoing description provides examples of embodiments of the urine temperature monitors 110, and embodiments of access point temperature-based screening systems, and does not limit the inventions, which are defined only by the appended claims. The scope of the inventions includes any modifications and supplementations that a person of ordinary skill in the art may perceive upon reading this disclosure. Further, the scope of the claimed inventions includes any equivalents that a well-informed court may provide under the doctrine of equivalents.

What is claimed is:

1. A device for estimating a core body temperature of a user, the device comprising:
    a heat trap shaped to receive a liquid stream and contain the thermal energy therein;
    said heat trap comprising low thermally conductive material;
    a temperature sensor in communication with a microprocessor, said temperature sensor associated with said heat trap and disposed proximate a surface of said heat trap, wherein said liquid stream is directed across said temperature sensor;
    wherein said heat trap comprises a sidewall including an upper section having an opening and a lower section having an outlet, said sidewall defining a perimeter around an enclosing the region, said enclosed region defining a passage for said liquid stream; and
    wherein said opening has a greater width than said outlet.

2. A device for estimating a core body temperature of a user, the device comprising:
    a heat trap shaped to receive a liquid stream and contain the thermal energy therein;
    said heat trap comprising low thermally conductive material;
    a temperature sensor in communication with a microprocessor, said temperature sensor associated with said heat trap and disposed proximate a surface of said heat trap, wherein said liquid stream is directed across said temperature sensor;
    said heat trap comprises a strip having a curvilinear cross-profile, said strip including a downwardly depending section adjacent to an upwardly depending section, said adjacent sections defining a partial perimeter and presenting a channel for said liquid stream.

3. A device for estimating a core body temperature of a user, the device comprising:
    a heat trap shaped to receive a liquid stream and contain the thermal energy therein;
    said heat trap comprising low thermally conductive material;
    a temperature sensor in communication with a microprocessor, said temperature sensor associated with said heat trap and disposed proximate a surface of said heat trap, wherein said liquid stream is directed across said temperature sensor;
    said heat trap comprises a strip including a downwardly depending section having at least one ridge rising from its surface, said ridge operable to alter liquid flow rate.

4. The device of claim 1, wherein said heat trap includes a thermally reflective surface.

5. The device of claim 1, wherein said heat trap further comprises a heat reflective surface.

6. The device of claim 1, wherein said heat trap further comprises a hydrophilic surface.

7. The device of claim 1, further comprising a second heat trap.

8. The device of claim 7, wherein said second heat trap is configured for selective distal placement relative to the first heat trap.

9. The device of claim 1, further comprising an alternately configured heat trap.

10. The device of claim 1, further comprising a processor and database configured to receive temperature input from said temperature sensor and associate said temperature input with a person.

11. The system of claim 1 further comprising an identity system.

12. The system of claim 11, wherein said identity system comprises an optical camera in communication with a person database, said optical camera enabling system comparison with the person database, facilitating identity information for a user.

13. The system of claim 11, wherein said identity system comprises an RFID reader in communication with a person database, said RFID reader providing identity information for a user.

14. The system of claim 11, wherein said identity system comprises a bar code reader in communication with a person database, said bar code reader providing identity information for a user.

15. The system of claim 11 wherein said identity system is selected from at least one of the following: an RF card system, a bar code system, a magnetic card system, an optical system, a smart card system, a biometric system, a hand scanner system, a fingerprint scanner system.

16. The device of claim 1, further comprising a processor and memory configured to receive input from said temperature sensor and compare said input with historical temperature records of a user.

17. The device of claim 1, further comprising a processor and memory configured to receive input from said temperature sensor and determine a febrile condition in response to said input.

18. The device of claim 1, further comprising a mount operable to secure the device to a toilet or adjacent surface.

* * * * *